(12) United States Patent  
Schwarz

(10) Patent No.: US 6,498,648 B1  
(45) Date of Patent: Dec. 24, 2002

(54) PROCEDURE FOR TAKING A REFERENCE MEASUREMENT

(75) Inventor: Peter Schwarz, Geretsried (DE)

(73) Assignee: BYK-Gardner GmbH, Geretsried (DE)

( * ) Notice: Subject to any disclaimer, the term of this patent is extended or adjusted under 35 U.S.C. 154(b) by 110 days.

(21) Appl. No.: 09/668,076

(22) Filed: Sep. 22, 2000

(30) Foreign Application Priority Data

Oct. 5, 1999 (DE) .......................................... 199 47 819

(51) Int. Cl.$^7$ .......................... G01N 21/55; G01B 11/00
(52) U.S. Cl. ....................................... 356/445; 356/388
(58) Field of Search ............................... 356/445, 402, 356/425, 388, 394; 250/226, 252.1

(56) References Cited

U.S. PATENT DOCUMENTS 5,691,817 A * 11/1997 Cargill et al. ................ 356/405
6,351,308 B1 * 2/2002 Mestha ........................ 356/402

\* cited by examiner

*Primary Examiner*—Michael P. Stafira
(74) *Attorney, Agent, or Firm*—Pearne & Gordon LLP

(57) ABSTRACT

Procedure for taking a reference measurement employing an optical device which comprises the following: an illuminating means having a source of radiation, its light being directed at a predetermined angle to a surface to be measured; a first optical measuring means which is aligned at a predetermined angle to said measurement surface and which receives a portion of the light reflected from said measurement surface and which comprises a photo sensor which emits a measurement signal characteristic of said reflected light; a second optical measuring means which is aligned at a predetermined angle to said measurement surface and which receives a portion of the light reflected from said measurement surface and which comprises a photo sensor which emits an electrical measurement signal characteristic of said reflected light; a control and evaluation means having a processor and memory means for controlling the measurement sequence and evaluating the measurement results which are then output via an output means. The procedure comprises the following steps: a reference surface is aligned with respect to the optical device and a measurement is taken by the first optical measuring means. A deviation parameter is determined from this measured value and a first stored calibration parameter. A measurement is then taken by the second optical measuring means and a second deviation parameter is derived from this measured value and a second stored calibration parameter. A variance parameter is derived from the first deviation parameter and the second deviation parameter, which is characteristic of the difference between the measured values of the first and the second optical measuring means. The measured value of the first measuring means is stored as the first reference parameter and the measured value of the second measuring means is stored as the second reference parameter or a warning signal is emitted when the variance parameter either exceeds or falls short of a predetermined range.

16 Claims, 4 Drawing Sheets

PROCEDURE FOR TAKING A REFERENCE MEASUREMENT

Figure 1:
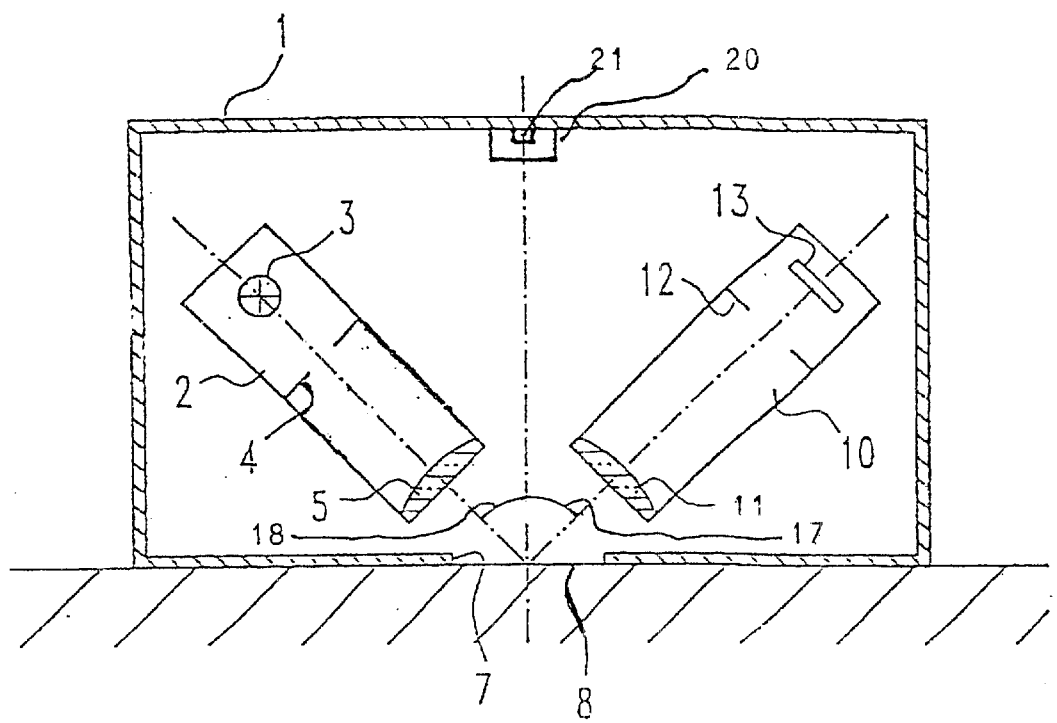

The present invention relates to a procedure for taking a reference measurement, respectively for recalibrating an optical measuring device used in determining surface quality.

Devices employed to determine the quality of surfaces of a wide variety of products are known in the prior art. Since surface quality is a crucial characteristic for many products in providing the total overall impression of the product, the quality of these products' surfaces often takes on special significance. For this reason, measuring devices are employed in order to qualitatively and quantitatively determine the visual properties of a surface.

Such measuring devices are exposed to dust and other contaminations in particular, but not limited thereto, in the production environment, causing the optics of such a device to become dirtied over the course of time, which in turn changes its transmission properties and may yield erroneous measurements. Therefore, conventional devices undergo routine maintenance at regular intervals.

Another problem arising in surface determinations is that individual elements in the devices age. Especially when using thermal light sources which include filaments, a portion of the filament will vaporize over time, settling on the inside of the surrounding glass bulb and changing the transmission characteristics of the glass bulb such that the light emitted from the light source will exhibit an age-induced spectral change.

The relative position of the light-radiating elements and the sensors to one another can also vary due to the effects of vibrations or jarring impacts, etc., so that the geometrical relational ratios within a measuring device can vary over the course of time.

Consequently, in order to obtain high quality measurements, many of the measuring devices known in the prior art are calibrated, respectively recalibrated, on a frequent basis. In so doing, the measuring device is placed on a surface having known properties and these properties are then determined with said measuring apparatus. The user can then balance or calibrate the device to zero, respectively to a particular deflection, for example by changing potentiometer resistance, so that any deviations in the devices can be compensated for to a certain extent.

To simplify operational handling, automatic calibration procedures are also known in the prior art which automatically recalibrate the measuring device to the corresponding reference value after a reference surface has been measured.

A disadvantage of the known prior art procedures and devices, however, is that many operator errors are not detected. A user frequently relies on the automatic mechanisms of such devices instead of, for example, scrutinizing the optical devices himself and controlling whether said devices are dirtied.

It is therefore the task of the present invention to provide a procedure as indicated above in order to enable making a reliable and reproducible reference measurement for calibrating or recalibrating an optical measuring device.

This task is solved in accordance with the present inventive procedure as defined in claim 1.

Further preferred embodiments of the invention constitute the subject matter of the subclaims.

A procedure according to the present invention for making a reference measurement is performed using an optical device which has at least a first illuminating means comprising at least one source of radiation and which is aligned at a predetermined angle to the measurement surface.

The optical device furthermore comprises at least a first and at least a second optical measuring means, both also aligned at a predetermined angle to the measurement surface and both receiving a portion of the light reflected from said measurement surface.

Both the first as well as the second optical measuring means in each case comprise at least one photo sensor which emits an electrical measurement signal which is in each case characteristic of the received, respectively reflected, light.

A control and evaluation means having at least one processor means and at least one memory means is additionally provided in the optical device in order to control the measurement sequence and to evaluate the measurement results. An output means is provided in the optical device for the outputting of the values.

The procedure according to the present invention using the optical device comprises the following steps which may be performed in the following or in a different order:

a) in a first step, the optical device and the reference surface are aligned with respect to one another; preferably, the optical device is placed upon the reference surface.

b) the first optical measuring means subsequently takes a measurement which is then preferably stored in the memory means.

c) a deviation parameter is derived from the measured value taken by the first measuring means and a first calibration value stored in the memory means which is characteristic of the first optical measuring means, said deviation parameter is a measure of the measured value's deviation from said first calibration parameter.

d) the next step entails the taking of a measurement with the second optical means.

e) after taking the measurement with the second measuring means, a second deviation parameter is derived from the measured value from said second measuring means and a second calibration parameter stored in the memory means which is characteristic of the second measuring means.

f) a variance parameter is derived from the first and the second deviation parameter, and g) a subsequent warning signal is issued when the variance parameter either exceeds or falls short of a certain range, or when the variance parameter is greater than a predetermined value.

The procedure according to the present invention has numerous advantages.

Upon employing the optical device for the first time, which usually takes place while still in the production or quality control stage, the device is first adjusted by means of measuring reference standards and making the corresponding precision fine-tuning.

High-quality measuring devices need to be recalibrated at regular intervals in order to essentially equalize, respectively exclude, any changes in geometric circumstances. Therefore, reference surfaces are provided for many measuring devices which have specifically known and defined properties; these reference surfaces may also correspond to the reference standards of the original precision adjustment.

In conventional measuring devices, at least within the scope of the final inspection or the precision adjusting stage, the measuring device is preferably placed upon at least one reference surface and the device then measures said reference surface. The relevant measured value is then stored as the calibration parameter in a memory of the measuring device, respectively printed in the product specification.

When such a measuring device needs to be recalibrated during the course of daily operation, it is then placed upon the relevant reference surface and measures the properties of said reference surface.

By comparing the values as thus determined with the calibration parameters stored in the memory means, respectively the printed calibration parameters, the device can be accordingly re-adjusted, thus allowing for a nullifying, at least to a certain extent, of effects as induced by contamination and other such similar factors.

However, it is frequently the case with measuring devices and procedures as known in the prior art for taking, respectively analyzing such a calibration or reference measurement, that these reference measurements are carried out incorrectly.

The procedure according to the present invention has the advantage with respect to the known methods that the measurement results of the first and of the second measuring means are subjected to a plausibility check, allowing for the avoiding of many erroneous reference, respectively calibration, measurements. It is not solely the problem that incorrect reference measurements need to be repeated in order to achieve high-quality meaningful measurement results, it is also the problem that many of these types of errors in reference or calibration measurements are only detected at a later point in time, meaning that, among other things, a number of measurements using the incorrect reference measurements may already been made in the ongoing production operations. Should such errors not be discovered until hours, days or even weeks later, a great number of flawed products may meanwhile have been manufactured during that time frame and to manufacture them anew translates into high expenditure. Neither can the damage to a company's image arising in the context of distributing flawed products be disregarded.

It is often the case with such types of measuring devices that one of its optics is defiled by, for example, a fingerprint while the other optic is essentially still unblemished. Such circumstances can be reliably determined with the procedure according to the present invention. First a measurement is taken by each optical measuring means during the course of the reference or calibration measurement and a deviation parameter is determined for each respective optics by means of a comparison with each respective calibration parameter stored in the memory means. In the cited example in which one of the optics is contaminated by, for example, a fingerprint, this means that the deviation parameter for this optic will be of a relatively high value while the deviation parameter for the unsullied optic will be small. A variance parameter, derived from the first and the second deviation parameter, will in this case therefore exhibit a relatively high value.

Thus, the procedure according to the present invention enables the quick and reliable determining of faulty reference measurements which may be due to, for example, partially soiled optics so that a warning signal can be emitted and the reference measurement can be re-taken, if necessary, following cleaning of the optics.

In a preferred embodiment of the procedure according to the present invention, at least one of the deviation parameters of the first or the second optical measuring means is derived from the difference between the measured value of the respective measuring means and the respective calibration value, whereby the first deviation parameter and the second deviation parameter in this case is preferably equal to the difference between the respective measured value and the first, respectively second, calibration parameter.

The forming of a deviation parameter from the difference between the measured value and the calibration value is advantageous since small deviations lead to small deviation parameters, while large deviations lead to accordingly larger deviation parameters.

In another preferred embodiment of the present inventive procedure, at least one deviation parameter, i.e., either the first deviation parameter or the second deviation parameter, is derived from a ratio between the corresponding measured value and the corresponding calibration value.

In a further preferred embodiment of one or several of the previously described embodiments, a warning signal is preferably emitted by said output means when the first and/or the second deviation parameter departs from a certain given range; i.e. exceeds or falls below a predetermined value.

This embodiment of the present inventive procedure is highly advantageous since other different possible errors can be reliably determined upon taking a reference or calibration measurement.

In this respect it may be possible, for example, that the illuminating means is dirty or that the radiation source in the illuminating means is defective, so that the radiation source is not emitting at any intensity or only very low intensity. Should a reference value in this case be taken with the first measuring means and the second measuring means, the measured signal will be very low; as a consequence, the error rate from this measurement sequence will be especially high. The deviation parameters derived from the measured values and the corresponding calibration parameters in this case are relatively large such that while both measuring means have, for example, a similar deviation and possibly only a small variance parameter has been determined, the error can be reliably detected in the reference measurement.

It is likewise possible, by means of limiting the deviation parameters, to reliably determine a flawed or contaminated reference surface. Should a reference surface be contaminated, this leads to lower measured values and without the procedure according to the present invention, would lead to an incorrect reference value and thus all subsequent measurements would likewise be faulty.

By the emitting of a warning signal upon one of the deviation parameters either exceeding or falling below an allowable range, contaminated reference measurement surfaces can be reliably detected.

It may furthermore be the case that a user employs an incorrect or unsuitable reference surface for calibration when making a reference measurement. These types of errors may also be essentially reliably avoided by means of limiting of a deviation parameter.

In a further preferred embodiment of the procedure according to the present invention, a warning signal is emitted when at least one of the measured values, taken with the first or the second measuring means while making the reference measurement, exceeds or falls short of a predetermined range.

This offers the advantage that the absolute measure of the individual measured values can be taken into consideration when assessing a reference measurement.

In all of the described embodiments, the first and/or the second deviation parameter can be derived from the original calibration parameter (from the initial precision adjustment) and the corresponding measured value.

It is also possible to derive the deviation parameter from the most recently saved calibration parameter (e.g. the measured value of the most recent valid reference measurement) and the current measured value.

In this variation, a measured value gradient is formed from that between the most recent reference measurement and the current measurement. A warning signal issues upon this gradient exceeding a predetermined and/or a selectable magnitude.

In a preferred embodiment of the present invention, the variance parameter is derived from the difference between the first and the second deviation parameter; in accordance with another embodiment, the variance parameter is derived from a ratio between the first and the second deviation parameter.

In another preferred embodiment of the present invention, the variance parameter is determined using a mathematic operation such as, for example, a linear, logarithmic or exponential calculation or other such similar calculations. Using a suitable mathematic operation allows for making even enhanced considerations of deviation parameters or measured values which, for example, exceed or fall short of a certain measure so that even further fine-tuned relevant assessments can be made with regard to the type of measurement (gloss, color, etc.).

In one or all of the previously described embodiments of the present invention, the optical device comprises a second illuminating means having at least one light source, its light directed at a predetermined angle to the measurement surface. According to the present preferred embodiment, it is especially preferred that the first illuminating means is arranged symmetrically to the first measuring means and especially preferred is that the second illuminating means is arranged symmetrically to the second measuring means.

It may however also be the case that the individual illuminating and measuring means are aligned at differing angles to the surface, whereby the predetermined angles at which the individual means (illuminating and measuring means) are aligned to the perpendicular of the surface to be measured can be angles of 0°, 5°, 10°, 15°, 20°, 30°, 40°, 45°, 50°, 60°, 70°, 75°, 80°, and 85° or other such similar angles. The arrangement of the angles when employing the inventive procedure also depends upon the measurement task the optical device is to perform.

In accordance with a preferred embodiment of the present invention, at least one of said deviation parameters, variance parameters and preferably measured reference values is stored essentially permanently in the memory means upon every reference measurement, whereby especially preferred is the essentially permanent storing in the memory means of at least the first and the second deviation and variance parameters.

This has numerous advantages in that the storing of the individual values also enables the taking of previous reference measurements into account when assessing the currently measured values, respectively deviation parameters, respectively variance parameters.

In accordance with a further preferred embodiment, a table means is provided in the memory means into which at least one of said parameters and preferably the first and the second deviation and variance parameters are essentially permanently stored on a line or similar object of said table for essentially each reference measurement. A measurement time parameter is preferably additionally stored upon each measurement. Thus the parameters from preceding reference measurements are essentially permanently available, and a warning signal can issue upon two consecutive reference measurements exhibiting a deviation, meaning for example a ratio or a difference between two consecutive parameters or measured values, which exceeds a predetermined magnitude.

As an example, a warning signal can be emitted when the deviation parameter from the $n^{th}$ reference measurement of one of the optics deviates by a certain amount from the deviation parameter from the $(n-1)^{th}$ reference measurement of the corresponding optics. Such a configuration also enables the inventive procedure to be applied with an optical device having only one optical measuring means. The previous reference measurements then serve as the reference measurement control and a warning signal is emitted when the measured value recorded from a reference measurement differs from the next reference measurement by an amount which is greater than a predetermined value. The applicants point out that they reserve the right to also claim protection for such a procedure.

In a further preferred embodiment of one or several of the previously described embodiments and configurations of the present invention when assessing a reference measurement, the table means provided in the memory means may be evaluated using statistical selective processes as are known in the prior art.

Should, for example, an offset line yield through linear regression of respectively each of the reference values of the first measuring means and the measured values of the second measuring means (when applicable), a reference measurement can be rejected, respectively a warning signal can be emitted when the current measured value deviates from said offset line by a predetermined measure.

This configuration enables that, for example, a slight increase in contamination can be tolerated as long as contamination does not reach too high of a measure. It simultaneously allows for reliably detecting errors in a reference measurement.

In all of the previously described configurations and embodiments, the warning signal is preferably emitted by the output means, whereby this task can ensue visually, acoustically or in another manner. It is also possible that the warning signal is emitted to a central device via radio or other similar means.

It is also possible that the inventive procedure is carried out using a device which has a plurality of three, four or more measuring means. Deviation parameters can then be determined for all or two, three or more of said measuring means.

Should a warning signal be emitted, the inventive procedure can decline acceptance of the measured value so that the user is required to, for example, re-confirm the value or first be required to eliminate the source of the error before a valid reference or calibration measurement will be accepted.

Figure 2:
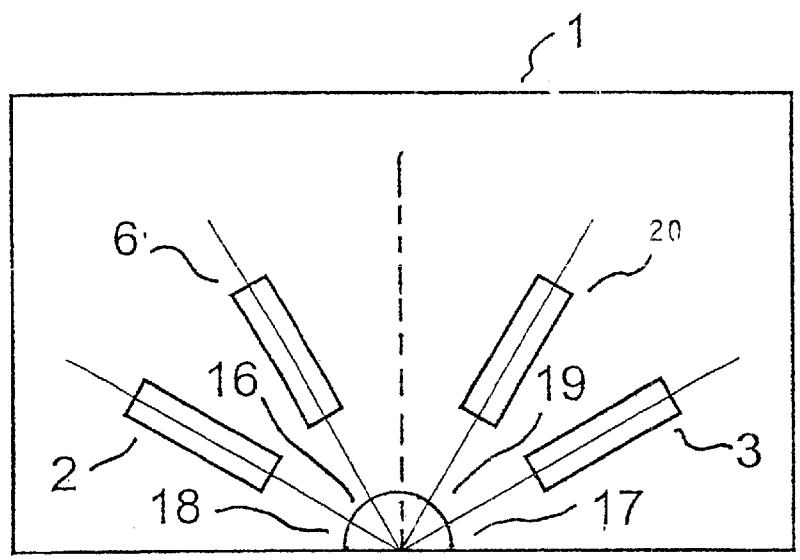
Figure 3:
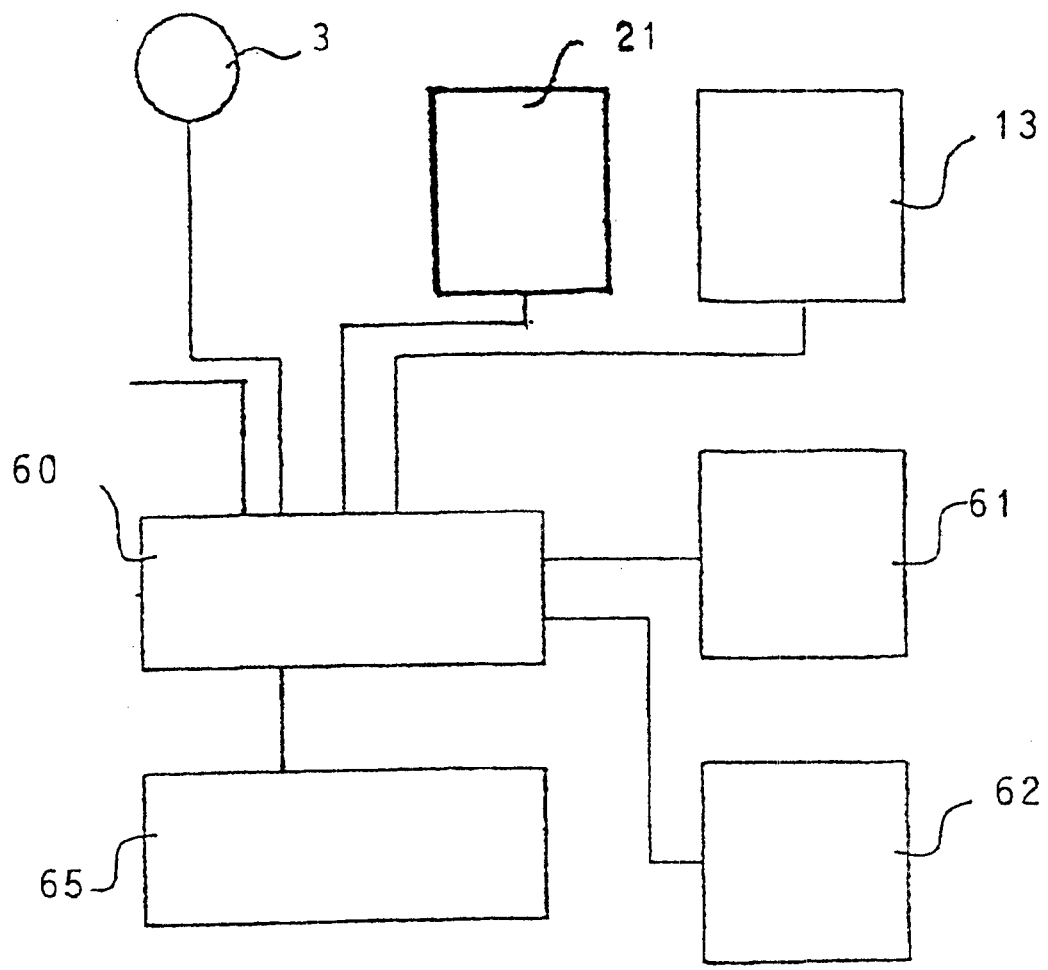
Figure 4A:
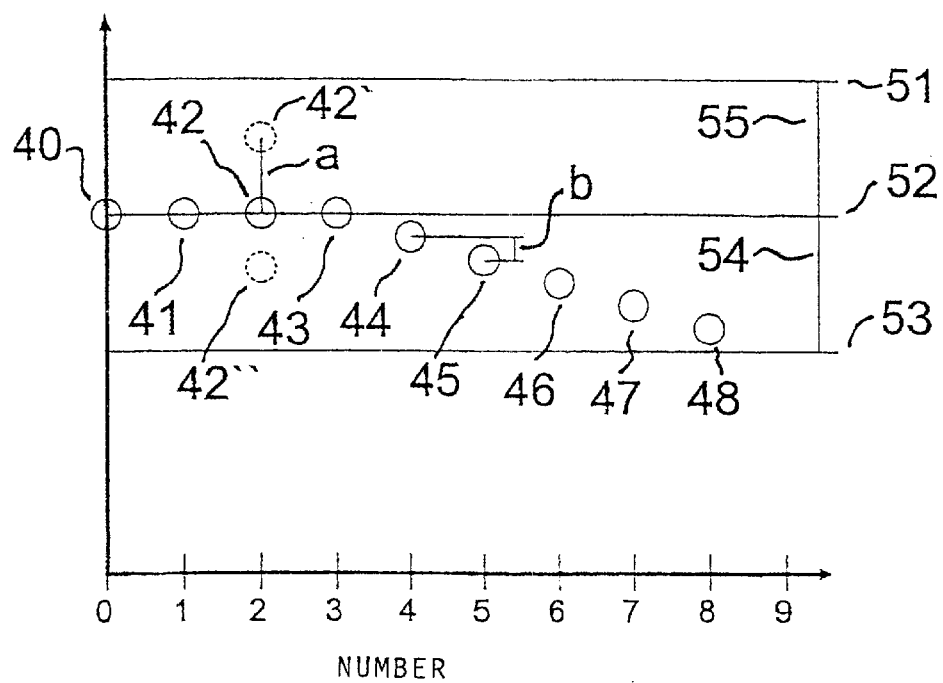
Figure 4B:
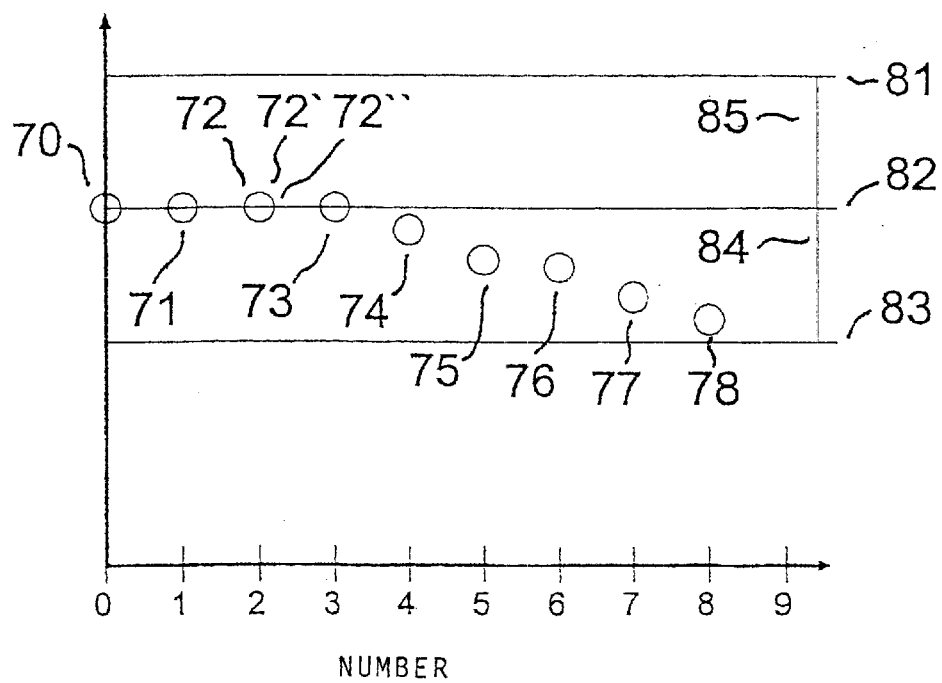
Figure 4C:
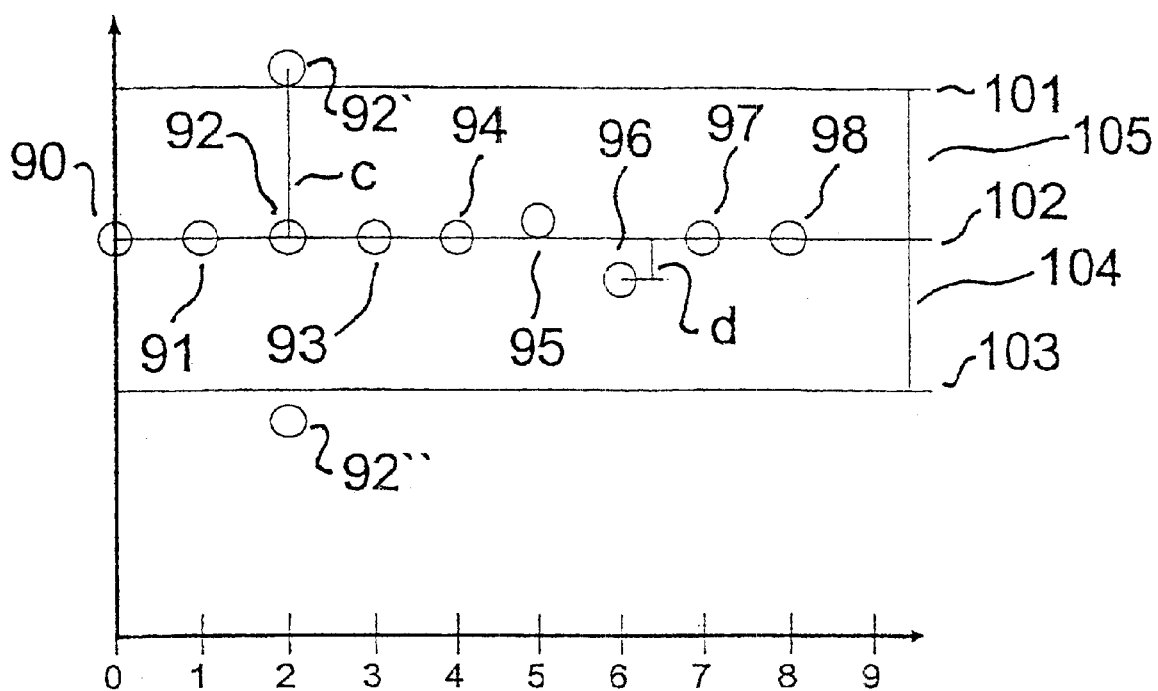

Further features and application possibilities of the present invention will now be specified in the following description of embodiments in association with the drawings, which show:

FIG. 1 a sectional view through a first embodiment of a device employed in the present inventive procedure;

FIG. 2 a sectional view through another optical device employed in conducting the present inventive procedure;

FIG. 3 the basic circuitry configuration of an optical device employed in conducting the present inventive procedure;

FIG. 4A the height of exemplary measured values from a number of reference measurements by the first measuring means;

FIG. 4B the height of the measured values of the reference measurements according to FIG. 4A by the second measuring means; and FIG. 4C the variance parameters of the reference measurements according to FIGS. 4A and 4B.

The procedure in accordance with the present invention will now be described with reference to the measuring devices illustrated in FIGS. 1 and 2. The measuring devices as represented in FIGS. 1 and 2 are used for the purpose of determining a surface's gloss. The inventive procedure can of course however also be employed with devices measuring color or other measuring devices for measuring other surface properties.

The gloss measuring device 1 illustrated in FIG. 1 comprises a first optical means 2 and a first measuring means 10, each aligned at a predetermined angle 17, 18 to measurement surface 8.

Illuminating means 2 comprises one or several light sources 3. An aperture 4 and a lens 5 is arranged In the path of radiation of illumination means 2 in order to direct the light emitted from the light source(s) essentially parallel onto measurement surface 8.

Said first measuring means 10 is provided with a lens 11 which focuses a portion of the light reflected from surface 8 onto a photo sensor 13 arranged in the first measuring means 10, whereby an aperture 12 is arranged in said first measuring means 10 for restricting opening.

A second measuring means 20 is furthermore arranged in said gloss measuring device which comprises a photo sensor 21. In the given embodiment, while said second measuring means 20 is configured in a simpler manner as said first measuring means 10, it can however comprise all the same elements as said first measuring means.

In contrast to the gloss measuring device illustrated in FIG. 1, the gloss measuring device illustrated in FIG. 2 comprises two illuminating means and correspondingly two measuring means. The reference numerals for identical or similar components have been maintained in FIG. 2.

The gloss measuring device according to FIG. 2 comprises a second illuminating means 6 which, in the present embodiment, is arranged symmetrically to the second measuring means 20.

The basic circuitry configuration illustrated in FIG. 3 may be employed with both gloss measuring devices.

The same electronics are preferably utilized for the controlling of the different optics and illuminating means and for the evaluating of measurement results in a measuring device. This offers the advantage that deviations in the electronics (due to environmental influences) will affect the different measurements in equal fashion.

A gloss measuring device used with the inventive procedure has a control and evaluation means 60 having at least one processor means. A program provided for the controlling of the device is stored in a memory means 61. Measured values, calibration values and other data may additionally be stored in said memory means 61. Said control means 60 serves to control light source(s) 3 and records the signals from photo sensors 13 and 21 in order to analyze same.

Output means 65 is configured as a display in order to emit visual warning signals. Output means 65 may also comprise a loudspeaker in order to emit acoustic warning signals.

The procedure according to the present invention will now be described with reference to FIGS. 4A, 4B and 4C.

FIG. 4A shows a number of measured values 40–48, 42', 42" from the first measuring means, which are based on the corresponding number of reference measurements.

A first reference measurement value 40 was recorded during or subsequent to manufacture of the device within the context of its precision fine-tuning and represents the original calibration parameter of said first measuring means.

FIG. 4B represents the corresponding measured values 70–78, 72' and 72", which correspond to the measured values as illustrated in FIG. 4A.

A number of limits and margins for errors are provided in the inventive procedure for the determining of errors, respectively for the avoiding of errors during calibration.

For example, a warning signal is issued when a measurement result from the first measuring means is ascertained to be above upper limit 51 of said first measuring means, respectively below lower limit 53 of said first measuring means. This avoids the accepting of a measurement result when, for example, due to a defective light source, only a low radiation is emitted. An upper limit 81 and a lower limit 83 is likewise provided for the second measuring means in order to similarly exclude such erroneous measurements.

When taking a reference measurement, respectively making calibrations, the gloss measuring device 1 is placed on reference surface 8 and a program stored in memory means 61 is started by means of inputting a control command via control component 62 of said gloss measuring device 1 and the color measuring device is controlled via control means 60 for taking the reference measurement.

Display 65 of device 1 preferably first prompts the user to place the gross measuring device on the reference surface to which recalibration is desired. A reference surface of this type may be, for example, disposed in (respectively integrated within) the housing of device 1 or a storage receptacle (not shown) for said device.

After placing said gloss measuring device 1 on reference surface 8 (the positioning procedure may be detected by means of a separate sensor (not shown)), the user may be prompted to start the calibration process by inputting a signal into input means 62.

First the light source of illuminating means 2 is switched on and a first measured value 41 is recorded. Following this step, in a device according to FIG. 1, another measured value 71 is recorded by second measuring means 20. With a gloss measuring device according to FIG. 2, in contrast, the second illuminating means 6 is activated and a measured value 71 is recorded by said second measuring means 20.

A deviation parameter is determined in each case from measured values 41, 71, determined as the difference between the respective original calibration parameters 40, 70 and the corresponding measured values 41, 71. In the example selected at present, with measured values 41 and 71, both the first deviation parameter as well as the second deviation parameter for the first, respectively second measuring means, are equal to zero since measured value 41 is equal to original calibration value 40 and since measured value 71 is equal to original calibration value 70.

Should the gloss measuring device now be recalibrated a second time immediately thereafter or after a certain period of time has elapsed, a measured value of, for example, 42' may be recorded by the first measuring means and a measured value of 72' may be recorded by the second measuring means. In this case, measured value 42' from the first measuring means exhibits a higher value than original calibration value 40 and measured value 41, yielding a first deviation parameter a as the difference between the current measured value and the preceding valid measured value 41. Measured value 72' as recorded by the second measuring means in this example exhibits the same value as the measured value of the preceding measurement 71 and the original calibration value 70, resulting in the second deviation parameter for the present measurement 72' being equal to zero.

Next, variance parameter 92' is formed from the difference between said first deviation parameter a of said first measuring means from measured value 42' and said second deviation parameter from measured value 72'.

In this example, measured value 42' deviates from the preceding measured value 41 by an amount of a, while measured value 72' of the second measuring means corresponds to measured value 71 from the preceding valid reference measurement.

A variance parameter derived from the difference between the two deviation parameters thus yields an amount of c, which corresponds to value 92' in FIG. 4C. In this example, measurement result 42' from first measuring means 10 deviates considerably more from the ideal measurement result 40, respectively 41, of said first measuring means than measured value 72' of said second measuring means does from the ideal measurement result 71, respectively 70 of said second measuring means.

In accordance with the inventive procedure, and in order to largely avoid the accepting of erroneous reference measurements, a variance parameter is derived from the measured values as is represented, for example, by reference numerals 90–98, 92' and 92" in FIG. 4C.

The determining of a variance parameter allows for the detecting of, for example, a case of dirtied optics. In this case, the measurement results from the first and the second measuring means will differ to a relatively large degree according to actual degree of contamination.

It is likewise possible that an inappropriate or incorrect reference surface is wrongly used so that the measurement results of one of the optical means may be displaced upwardly or downwardly due to the surface properties of the corresponding surface. It is likewise possible that an error may occur in carrying out a reference measurement from the fact of the measuring device being set upon the reference surface to be measured at a angle.

With a gloss measuring device as illustrated in FIG. 2, the different measuring means are directed at different angles to the surface so that a tilting of the positioning angle affects the two measuring means to greatly differing degrees. Such a tilting error usually results in lower measured values being determined. In certain circumstances (e.g. with structured surfaces or surfaces having a certain roughness) higher measured values may also be determined.

Measured value 42' in FIG. 4A can serve as an example of such a tilting error which results from the fact that the measuring means is directed at a greater angle than intended to, for example, a structured measurement surface.

While the measurement surface is slightly tilted when measuring with the first measuring means, for example, and thus attaining a higher value 42' than the ideal value 40, respectively 41, the measurement with the second measuring means 20 is measured correctly so that a correct measured value 72' is obtained. In this example, variance parameter 92' as the difference between the deviation parameters (difference of the differences between the current measurement values and the correspondingly valid reference values) exceeds the upper valid range 101 for the variance parameter, resulting in a warning signal being emitted and the user being prompted to repeat the reference measurement. A warning signal is issued even though measured value 42' is still within the valid range between upper limit 51 and lower limit 53 for the reference measurement values of the first measuring means.

Measured value 42' is rejected and the reference measurement must be repeated. The subsequent reference measurement returns measured value 42" from the first measuring means and measured value 72" from the second measuring means. While measured value 72" is correctly determined, measured value 42" exhibits too low of a magnitude. This can be attributed, for example, to soiled optical components in the first measuring means. The variance parameter 92" determined from the measured values is below lower limit 103 of the variance parameter's valid range and thus the reference measurement will be rejected and must be repeated, even though measured value 42" is still within the range of validity for the reference measurement values of said first measuring means. The magnitude of measured values 42" and 72" allow for the detecting of slightly dirtied optics in the present example and can basically exclude that measured values 42" and 72" were determined with an inappropriate or incorrect reference surface.

The subsequently measured value 42 meets the requisite conditions and is accepted, just as reference measurement value 72 is.

The procedure according to the present invention enables a relatively high restricting of the allowable deviations between the first measuring means and the second measuring means whereby increasing signs of aging and/or contamination in the relevant components involved can be tolerated to a certain degree. This is shown by the further reference measurements 43, 44, 45, 46, 47, 48, as taken by the first measuring means and the corresponding measured values 73, 74, 75, 76, 77, 78 taken by the second measuring means.

The corresponding variance parameters 93, 94, 95, 96, 97, 98 of said reference measurements are represented in FIG. 4C. While the recorded intensity of the first and the second measuring means decreases over the course of time, respectively with an increasing number of reference measurements made, the corresponding variance parameters 93–98 remain within the allowable range between the variance parameters' lower limit 103 and the variance parameters' upper limit 101.

The range of allowable variance parameters may also be expressed by an ideal variance parameter 102 (differences derived preferably from a value of zero) and an allowable positive deviation 105 and an allowable negative deviation 104, whereby the ranges of positive and negative deviations do not have to be symmetrical.

While the recorded intensity steadily decreases from measured value 73 of the second measuring means to measured value 78 of said second measuring means, measured values 75 and 76 deviate from a linear decline. In contrast, a linear decline does occur across example measured values 43–48 as represented in FIG. 4a.

Bulb quality can be ascertained from the changes seen in measured values 41–48 over time and a further warning signal can be emitted when, for example, the change (per measurement or over time) is deemed too great. Replacing the light source may then also be recommended.

The variance parameters 93–98 determined from measured values 43–48 and the corresponding measured values 73–78 of the second measuring means are all above the variance parameters' lower allowed limit 103 and below the variance parameters' upper allowed limit 101.

To determine the deviation parameter of the first and the second measuring means, it is also possible to determine the difference between the current measured value and the most recently determined valid reference measurement value of the corresponding measuring means, which yields deviation parameter value b (gradient formation).

An upper and lower limiting is likewise set for said deviation parameter value b, in order to prevent too great of a variation between two consecutive reference measurements.

What is claimed is:

1. Method for taking a reference measurement comprising:

a) providing an optical measuring device comprising at least one illuminating means, a first optical measuring means and a second optical measuring means;
b) arranging a reference surface and the optical measuring device with respect to one another;
c) taking a measurement with the first optical measuring means;
d) deriving a first deviation parameter from the measured value of said first optical measuring means and a first calibration parameter;
e) taking a measurement with the second optical measuring means;
f) deriving a second deviation parameter from the measured value of said second optical measuring means and a second calibration parameter; and
g) deriving a variance parameter from said first deviation parameter of said first optical measuring means and said second deviation parameter of said second optical measuring means, whereby said variance parameter is characteristic of the difference between said first and said second deviation parameters.

2. Method according to claim 1, wherein at least one of said first and said second deviation parameters is determined from the difference between said measured value of the respective measuring means and the corresponding calibration parameter.

3. Method according to claim 1, wherein at least one of said first and said second deviation parameters is determined from a ratio between said measured value of the respective measuring means and the corresponding calibration parameter.

4. Method according to claim 1, wherein a warning signal is emitted when said first deviation parameter departs from a predetermined range for said first measuring means and/or when said second deviation parameter departs from a predetermined range for said second measuring means.

5. Method according to claim 1, wherein a warning signal is emitted when said variance parameter exceeds or falls below a predetermined range.

6. Method according to claim 1, wherein said variance parameter is derived from the difference between said first and said second deviation parameters.

7. Method according to claim 1, wherein said variance parameter is derived from a ratio between said first and said second deviation parameters.

8. Method according to claim 1, wherein said variance parameter is determined using a mathematical operation selected from the group of operations consisting of linear operations, logarithmic operations and exponential operations.

9. Method according to claim 1, said optical measuring device further comprising a second illuminating means having at least one light source with its light being directed at a predetermined angle to said reference surface.

10. Method according to claim 1, wherein said illuminating means, said first measuring means and/or said second measuring means is aligned at a predetermined angle relative to said reference surface, said angle being selected from the group consisting of angles measuring 0°, 5°, 10°, 15°, 20°, 30°, 40°, 50°, 60°, 70°, 75°, 80°, and 85°.

11. Method according to claim 1, wherein said illuminating means is arranged symmetrically to said first measuring means.

12. Method according to claim 1, wherein at least one value selected from the group of values consisting of said first and said second deviation parameters, said variance parameter, said measured value of said first measuring means, and said measured value of said second measuring means, is stored essentially permanently in a memory means of said optical measuring device.

13. Method according to claim 1, wherein said measured value of said first measuring means is stored as a first calibration parameter of said first measuring means and/or said measured value of said second measuring means is stored as a second calibration parameter of said second measuring means.

14. Method according to claim 1, wherein a first predetermined angle at which said first measuring means is aligned to said reference surface, and a second predetermined angle at which said second measuring means is aligned to said reference surface are dissimilar.

15. A method according to claim 1, further comprising performing a plausibility check using said variance parameter to determine whether said first or said second measuring means is functioning properly.

16. A method according to claim 1, wherein geometric changes in said optical device are detected.

* * * * *

UNITED STATES PATENT AND TRADEMARK OFFICE
CERTIFICATE OF CORRECTION

PATENT NO.     : 6,498,648 B1                                              Page 1 of 1
DATED          : December 24, 2002
INVENTOR(S)    : Peter Schwartz It is certified that error appears in the above-identified patent and that said Letters Patent is hereby corrected as shown below:

<u>Title page,</u>
Item [30], Foreign Application Priority Data, please delete "199 47 819", and insert therefor -- 199 47 819.8 --.

<u>Column 1,</u>
Line 59, please delete "This task is solved in accordance with the present inventive procedure as defined in claim 1.".
Line 61, please delete "Further preferred embodiments of the invention constitute the subject matter of the subsclaims.".

Signed and Sealed this

Tenth Day of June, 2003

JAMES E. ROGAN
*Director of the United States Patent and Trademark Office*